United States Patent
Narita et al.

[11] Patent Number: 5,132,429
[45] Date of Patent: Jul. 21, 1992

[54] BENZOTRIAZOLE DERIVATIVES AND FLUORESCENCE-EMITTING REAGENTS THEREOF

[75] Inventors: Shigeru Narita; Takayasu Kitagawa, both of Osaka, Japan

[73] Assignee: Shionogi & Co., Ltd., Osaka, Japan

[21] Appl. No.: 613,754

[22] PCT Filed: May 25, 1989

[86] PCT No.: PCT/JP89/00518
§ 371 Date: Nov. 20, 1990
§ 102(e) Date: Nov. 20, 1990

[87] PCT Pub. No.: WO89/12044
PCT Pub. Date: Dec. 14, 1989

[30] Foreign Application Priority Data
May 31, 1988 [JP] Japan .................. 63-134835

[51] Int. Cl.$^5$ ........................... C07D 249/18
[52] U.S. Cl. ..................... 548/257; 548/261; 544/132; 544/366; 436/800; 546/199
[58] Field of Search ........... 548/259, 257, 260, 261

[56] References Cited

U.S. PATENT DOCUMENTS

| | | | |
|---|---|---|---|
| 2,136,135 | 11/1938 | Johner et al. | 548/259 |
| 3,860,604 | 1/1975 | Model et al. | 548/261 |
| 4,182,713 | 1/1980 | Goebel et al. | 548/259 |
| 4,272,298 | 6/1981 | Bäbler | 548/257 |
| 4,533,612 | 8/1985 | Eilingsfeld et al. | 548/257 |
| 5,003,076 | 3/1991 | Narita et al. | 548/257 |

FOREIGN PATENT DOCUMENTS

0131292 1/1985 European Pat. Off. ......... 548/257
89-12044 12/1989 PCT Int'l Appl. ............. 548/257

OTHER PUBLICATIONS

Narita et al., Chem. Pharm. Bull. vol. 37 1009-12 (1989).
Chem. Abstr. vol. 112, Entry 178992u (1990) abstracts WO8912044.
Chem Abstr. vol. 112 Entry 32813q (1990).
Narita et al. Chem. Abstr. vol. 111 entry 32998h (1989).

*Primary Examiner*—Donald G. Daus
*Attorney, Agent, or Firm*—Wenderoth, Lind & Ponack

[57] ABSTRACT

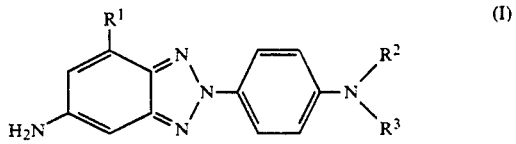

The invention relates to compounds represented by formula (I) and their salts: wherein $R^1$ represents hydrogen, lower alkyl, halogen, cyano, or lower alkyloxycarbonyl, $R^2$ and $R^3$ each represents hydrogen, lower alkyl, $C_3$–$C_7$ cycloalkyl, or aryl, or taken together may form piperazino or morpholino together with the adjacent nitrogen atom. These compounds scarcely emit fluorescence when present alone in an aqueous solution but, in the presence of a protein such as $\alpha_1$-AG, they bind to the protein to emit strong fluorescence, thus being suitable reagents for determining proteins existing in a minute amount in blood, particularly $\alpha_1$-AG.

2 Claims, 1 Drawing Sheet

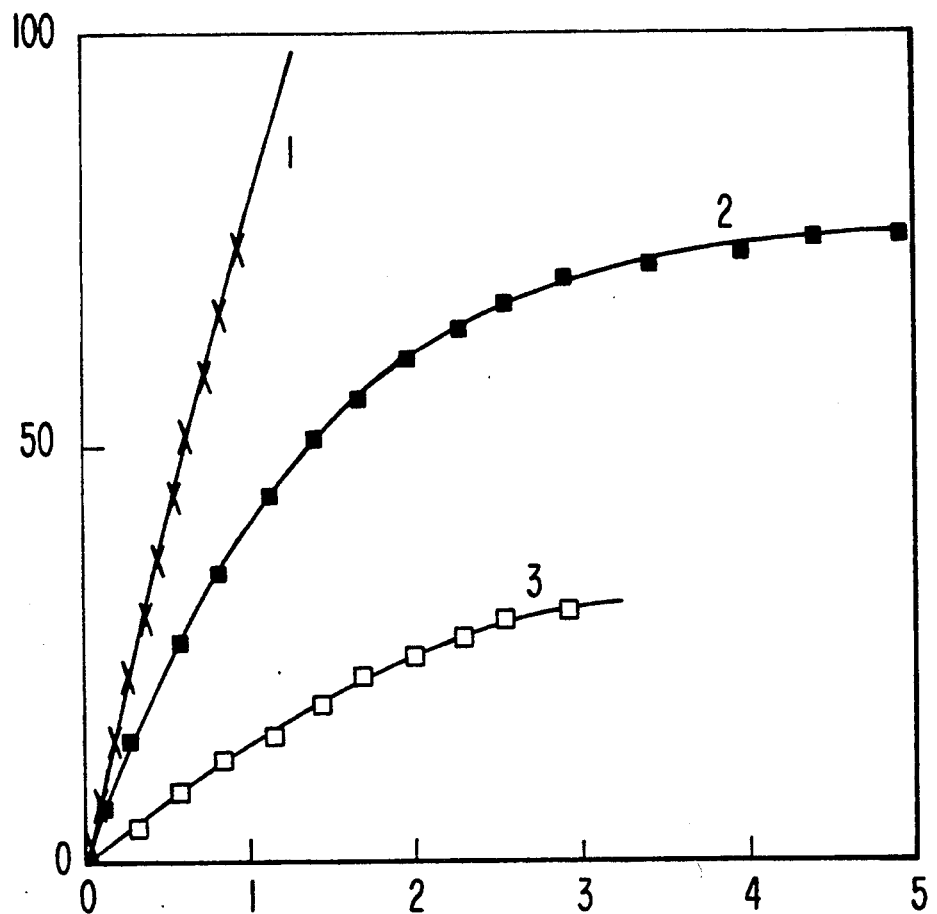

BENZOTRIAZOLE DERIVATIVES AND FLUORESCENCE-EMITTING REAGENTS THEREOF

FIELD OF THE INVENTION

This invention relates to reagents for analysis of protein-binding, which are suitable for estimating the binding strength between a drug and a protein, especially between a basic drug and $\alpha_1$-acid glycoprotein (hereafter referred to as $\alpha_1$-AG).

BRIEF EXPLANATION OF THE DRAWING

The drawing indicates the relationship of concentration versus fluorescence intensity, where the abscissa shows concentrations of the compound 1 ($\times 10^{-6}$M) and the ordinate shows fluorescence intensity (%).

BACKGROUND OF THE INVENTION

It is important to estimate quantitatively the binding strength of a drug to serum protein in the explication of drug behaviors in the living body. Recently much attention has been paid to $\alpha_1$-AG as a bound protein to a basic drug in blood and reports on the interaction of $\alpha_1$-AG with a wide variety of drugs are increasing. The fluorescence probe method, one of the methods for estimating protein-binding strength, is highly sensitive and easy to handle, however, it is hard to say that known fluorescence probes are suitable for the estimation of the binding strength to $\alpha_1$-AG. For example, Auramin O and Phenprocoumon etc. are known and reported as fluorescence probes for $\alpha_1$-AG. The former, which is disclosed in Y. Sugiyama et al, Biochem. Pharmcol. 34(6), 821-829 (1985), has a demerit of low sensitivity in determining a very small quantity of a protein, because the binding strength of it to $\alpha_1$-AG is very weak. The latter, which is disclosed in M. Otagiri et al., J. of Pharmaceutical Sciences 76(8), 646-649 (1987), has also some demerits that it is easily effected by fluorescence of a protein itself, because its wavelength suitable for determination is short.

DISCLOSURE OF THE INVENTION

In view of the circumstances above, the present inventors have tried to develop a fluorescence probe which has a high affinity with a protein, especially $\alpha_1$-AG, and is capable of determination at long wavelength, whereby they completed this invention.

Benzotriazole derivatives, which are provided by this invention and shown by the following formula:

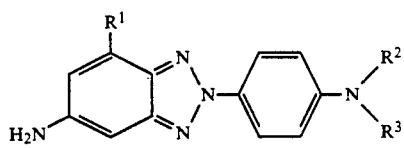

wherein $R^1$ is hydrogen, lower alkyl, halogen, cyano, or lower alkyloxycarbonyl, $R^2$ and $R^3$ each is hydrogen, lower alkyl, $C_3$-$C_7$ cycloalkyl, or aryl, or taken together may form $C_3$-$C_7$ alkylene or may form piperazino or morpholino together with the adjacent nitrogen atom, or a salt thereof (hereafter referred to simply as the compounds of this invention), these compounds per se scarcely emit fluorescence in an aqueous solution, while in the presence of a protein such as $\alpha_1$-AG they bind to the protein to emit strong fluorescence. The compounds of this invention compete with a wide variety of basic drugs at the same site on a protein and, at that time, the change in fluorescence intensity can be obserbed. From this change of fluorescence intensity, exact determination with simplicity can be performed by estimating the binding strength of the drug to a protein by means of known fluorescence probe methods.

Since the compounds of this invention have, as mentioned before, a very high binding affinity for a protein, quantitative determination of a minute amount of a protein in blood, especially $\alpha_1$-AG, can also be performed easily.

Benzotriazole derivatives provided by this invention can be prepared easily by reactions known in the field of organic chemistry. For example, as shown below, a 5-substituted metaphenylenediamine (a) is subjected to known diazo coupling reaction with a paraphenylenediamine derivative (b) (Step 1), then to ring-closing reaction (Step 2), to give the compounds of this invention.

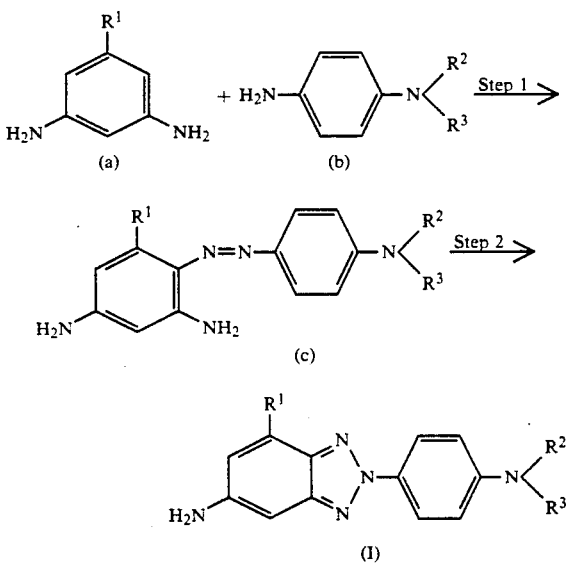

In the reaction scheme, $R^1$, $R^2$, and $R^3$ each has the same meaning as defined above.

The process above is explained below step by step.

Step 1

The reaction is usually carried out in an aqueous solution at a temperature from ice-cooling to 15° C. The compound (b) is dissolved or suspended in an inorganic acid, which is then reacted with nitrous acid such as sodium nitrite to obtain a highly reactive diazo compound. Sulfamic acid or urea is added thereto to remove the excessive nitrous acid.

Next, the compound (a) is added thereto, whereby it is easily coupled with the diazo compound to give the compound (c). The reaction is completed in several minutes to several hours.

Step 2

The azo group of the compound (c) easily reacts with the adjacent amine intramolecularly to give the compounds of this invention (I). The reaction is completed in several minutes to several ten hours at room temperature or under heating, if carried out in a water-containing organic solvent in the presence of a copper-ammonia complex.

In this invention, halogen means fluoro, chloro, or bromo. Lower alkyl means a straight or branched chain $C_1$-$C_5$ alkyl, including methyl, ethyl, n-propyl, isopropyl, n-butyl, sec-butyl, tert-butyl, n-pentyl, isopentyl, neopentyl, and tert-pentyl, etc.

$C_3$-$C_7$ cycloalkyl means cyclopropyl, cyclobutyl, cyclopentyl, cyclohexyl, cycloheptyl, which may have one or two substituents such as halogen, lower alkyl, lower alkyloxy.

Aryl means a phenyl group which may have one or two substituents, and includes, for example, phenyl, tolyl, xylyl, cumenyl, o-, m-, p-chlorophenyl, etc.

$C_3$-$C_7$ alkylene includes propylene, butylene, pentylene, hexylene, heptylene etc.

The representative examples of the compounds of this invention are listed below, which do not limit the scope of this invention.

(1) 7-chloro-2-(p-diethylaminophenyl)-2H-benzotriazolyl-5-amine,
(2) 7-chloro-2-(p-methylaminophenyl)-2H-benzotriazolyl-5-amine,
(3) 7-chloro-2-(p-anilinophenyl)-2H-benzotriazolyl-5-amine,
(4) 7-chloro-2-(p-morpholinophenyl)-2H-benzotriazolyl-5-amine,
(5) Ethyl 6-amino-2-(p-diethylaminophenyl)-2H-benzotriazole-4-carboxylate,
(6) 2-(p-cyclohexylaminophenyl)-2H-benzotriazolyl-5-amine,
(7) 7-cyano-2-(p-piperidinophenyl)-2H-benzotriazolyl-5-amine,
(8) 7-bromo-2-(p-cyclopropylaminophenyl)-2H-benzotriazolyl-5-amine,
(9) 7-chloro-2-(p-piperazinophenyl)-2H-benzotriazolyl-5-amine, and
(10) Methyl 6-amino-2-(p-diisopentylaminophenyl)-2H-benzotriazole-4-carboxylate.

By using the compounds of this invention above, (1) the binding strength of a drug to a protein and (2) the amount of protein in blood can be determined easily and precisely. The procedures for analysis are explained simply in the following Examples.

(1) DETERMINATION OF BINDING STRENGTH OF DRUG TO PROTEIN

Binding Strength of Basic Drug to $\alpha_1$-AG

Two different kinds of solutions, one containing $\alpha_1$-AG and a compound of this invention listed above, the other containing $\alpha_1$-AG, the compound of this invention, and a drug, are prepared to measure fluorescence intensity at the excitation. fluorescence wavelength, as shown in Table 2. According to the working curve made beforehand, the binding rate of the compound to $\alpha_1$-AG in each solution is determined and the binding constant of a drug to $\alpha_1$-AG is calculated from the difference between the binding rates in the presence and the absence of a drug.

(2) QUANTITATIVE DETERMINATION OF PROTEIN IN BLOOD

Quantitative Determination of Albumin

A solution containing a compound is added to a solution containing albumin and the mixed solution is subjected to determination of fluorescence intensity at excitation. fluorescence wavelength as shown in Table 2. According to the working curve on the standard albumin solution made beforehand, the concentration of albumin in the sample solution is determined.

Quantitative Determination of $\alpha_1$-AG

Sulfosalicylic acid is added to the sample solution containing $\alpha_1$-AG to remove coexisting proteins, to which the solution containing a compound is added. The mixed solution is subjected to determination of fluorescence intensity at excitation. fluorescence wavelength as shown in Table 2. According to the working curve on the standard solution of $\alpha_1$-AG, the concentration of $\alpha_1$-AG in the sample is determined.

The invention is further explained in the following Examples and Experiments, which are not intended to limit the scope of this invention.

EXAMPLE

The compounds of this invention 1-5 were prepared as shown in the following Examples 1-5. Physical constants on each compound are shown on Table 1.

EXAMPLE 1

Preparation of 7-chloro-2-(p-diethylaminophenyl)-2H-benzotriazolyl-5-amine(1)

A 10% aqueous solution (7 ml) of sodium nitrite was added to a solution of N,N-diethyl-p-phenylenediamine dihydrochloride (10 mmol) dissolved in 50 ml of 10% hydrochloric acid, while being stirred under ice-cooling. Fifteen minutes later, 10% ammonium sulfamate (15 ml) was added thereto and the mixture was stirred for 15 minutes. The reaction mixture was adjusted to about pH 5 with sodium acetate, then 5-chloro-m-phenylenediamine (10 mmol) was added thereto and the resulting mixture was stirred for 2 hours.

The reaction mixture was adjusted to about pH 9 with 1N sodium hydroxide, then extracted with ethyl acetate. The ethyl acetate layer was evaporated to leave a residue, which was dissolved in pyridine (40 ml), then an ammoniacal cupric sulfate solution which was prepared by dissolving 10 g of cupric sulfate pentahydrate in 60 ml of 14% ammonia was added thereto and the resulting mixture was refluxed for 4 hours. Next, after cooling the reaction solution, the resulting mixture was extracted with ethyl acetate. The ethyl acetate layer was dried over anhydrous sodium sulfate and evaporated under reduced pressure to leave a residue, which was dissolved in ethyl acetate (5 ml), then the resulting mixture was purified by using a silicagel chromatography with ethyl acetate as eluent, whereby the objective compound 1 was obtained.

EXAMPLE 2

Preparation of 7-chloro-2-(p-methylaminophenyl)-2H-benzotriazolyl-5-amine(2)

The reaction was performed according to the same manner as in Example 1, except that N-methyl-p-phenylenediamine dihydrochloride was used in place of N,N-diethyl-p-phenylenediamine dihydrochloride, whereby the objective compound 2 was obtained.

EXAMPLE 3

Preparation of
7-chloro-2-(p-anilinophenyl)-2H-benzotriazolyl-5-amine(3)

The reaction was performed according to the same manner as in Example 1, except that N-phenyl-p-phenylenediamine dihydrochloride was used in place of N,N-diethyl-p-phenylenediamine dihydrochloride, whereby the objective compound 3 was obtained.

EXAMPLE 4

Preparation of
7-chloro-2-(p-morpholinophenyl)-2H-benzotriazolyl-5-amine(4)

The reaction was performed according to the same manner as in Example 1, except that p-morpholinoaniline was used in place of N,N-diethyl-p-phenylenediamine dihydrochloride, whereby the objective compound 4 was obtained.

EXAMPLE 5

Preparation of Ethyl
6-amino-2-(p-diethylaminophenyl)-2H-benzotriazole-4-carboxylate(5)

The reaction was performed according to the same manner as in Example 1, except that Ethyl 3,5-diaminobenzoate dihydrochloride was used in place of 5-chloro-m-phenylenediamine, whereby the objective compound 5 was obtained.

The reagents of this invention for analysis were prepared as shown in the following Examples 6–10.

EXAMPLE 6

$1 \times 10^{-5}$M Aqueous Solution

To a solution of the compound 1 (31.6 mg) dissolved in 0.1N hydrochloric acid (10 ml) was added a necessary amount of water to make the whole 10 L. This was distributed into brown vials by 5 ml each, then sealed hermeticaly to give the reagent for analysis.

EXAMPLE 7

$1 \times 10^{-5}$M Methanol Solution

To a solution of the compound 2 (27.4 mg) dissolved in methanol (10 ml) was added a necessary amount of water to make the whole 10 L. This was distributed into brown vials by 5 ml each, then sealed hermeticaly to give the reagent for analysis.

EXAMPLE 8

$1 \times 10^{-5}$M Ethanol Solution

The reagent for analysis was obtained according to the same manner as in Example 7, except that 33.6 mg of the compound 3 and ethanol were used.

EXAMPLE 9

$1 \times 10^{-4}$M Aqueous Solution

The reagent for analysis was obtained according to the same manner as in Example 6, except that 33.0 mg of the compound 4 was used.

EXAMPLE 10

$1 \times 10^{-4}$M Methanol Solution

The reagent for analysis was obtained according to the same manner as in Example 7, except that 35.3 mg of the compound 5 was used.

TABLE 1

| No | Appearance IR (Nujol) | m.p. (°C.) | Molecular Formula | Elementary Analysis (Calcd./Found) | | | |
|---|---|---|---|---|---|---|---|
| | | | | C | H | N | Cl |
| 1 | orange plates 3230, 3340, 3440 | 187–188 | $C_{16}H_{18}N_5Cl$ | 60.85 61.00 | 5.75 5.86 | 22.18 22.02 | 11.23 11.06 |
| 2 | light brown plates 3220, 3330, 3415 | 211–213 | $C_{13}H_{12}N_5Cl$ | 57.04 57.10 | 4.42 4.52 | 25.59 25.35 | 12.95 12.84 |
| 3 | brown plates 3210, 3360 3400, 3480 | 174–175 | $C_{18}H_{14}N_5Cl$ | 64.38 64.62 | 4.20 4.36 | 20.86 20.61 | 10.56 10.60 |
| 4 | yellow needles 3230, 3360, 3480 | 246–247 | $C_{16}H_{16}N_5OCl$ | 58.27 58.35 | 4.89 4.98 | 21.24 21.11 | 10.75 10.75 |
| 5 | dark prism 1713, 3230 3360, 3450 | 146–148 | $C_{19}H_{23}N_5O_2$ | 64.57 64.85 | 6.56 6.74 | 19.82 19.51 | — — |

TABLE 2

| | $\alpha_1$-AG | | Human Serum Albumine | |
|---|---|---|---|---|
| No | Excitation Wavelength (nm) | Fluorescence Wavelength (nm) | Excitation Wavelength (nm) | Fluorescence Wavelength (nm) |
| 1 | 418 | 508 | 415 | 505 |
| 2 | 396 | 482 | 385 | 480 |
| 3 | 400 | 505 | 400 | 485 |
| 4 | 396 | 502 | 383 | 465 |
| 5 | 452 | 567 | 420 | 520 |

EXAMPLE 11

Determination of Binding Constant of Chloropromazine

Experiment 1

In the fluorescence cell made of quartz with a plug was placed the buffer solution of 0.1M phosphoric acid (2 ml) which pH is 7.4 and containig $1 \times 10^{-4}$M $\alpha_1$-AG, to which $5 \times 10^{-4}$M aqueous solution of the compound 1 was added by 2 μl each with a microcylinder, which was prepared by dissolving about 3 mg of the compound 1 in 1N hydrochloric acid (1 ml), followed by diluting with water to make the total volume 200 times, and the resulting solution was mixed fully to determine fluorescence intensity at 508 nm (excitation wavelength: 418 nm). In this case, all of the compound 1 bound to $\alpha_1$-AG and the relationship of concentration versus fluorescence intensity became as the linear 1 shown in the drawing.

Experiment 2

For the buffer solution of 0.1M phosphoric acid (2 ml) which pH is 7.4 and containing $3 \times 10^{-6}$M $\alpha_1$-AG, the same procedure as in Example 1 was performed. In this case, the binding of the compound 1 to $\alpha_1$-AG was under an equilibrium condition and the relationship of concentration versus fluorescence intensity became as the curve 2 shown in the drawing.

Experiment 3

For the buffer solution of 0.1M phosphoric acid (2 ml) which pH is 7.4 and containing $1 \times 10^{-6}$M chloropromazine and $3 \times 10^{-6}$M $\alpha_1$-AG, the same procedure as in Example 1 was performed. In this case, the binding of the compound 1 to $\alpha_1$-AG was inhibited by chloropromazine and the relationship of concentration versus fluorescence intensity became as the curve 3 shown in the drawing.

Method of Calculation

The binding rate (X) of the compound 1 to $\alpha_1$-AG was introduced from the following formula (1)

$$X = \frac{Fp - Fo}{Fb - Fo} \tag{1}$$

In this scheme, Fb is fluorescence intensity at some concentration of the compound 1 which was obtained in Experiment 1, Fp is fluorescence intensity at the same concentration of the compound 1 which was obtained in Example 2, and Fo is blank value.

The value introduced from the binding rate at each concentration of the compound 1 was plotted accoding to the formula (2) of Scatchard, whereby the binding parameter of the compound 1 to $\alpha_1$-AG was obtained.

$$r/Df = nKa - rKa \tag{2}$$

In this scheme, r is the amount of binding of the compound 1 per $\alpha_1$-AG (1 mole), n is the number of binding site, Ka is the binding constant of the compound 1, Df is the concentration of the compound 1 which is free form. The binding parameters of the compound 1 for $\alpha_1$-AG were Ka=$1.46 \times 10^{-6}$M$^{-1}$, n=0.40.

The binding constant of chloropromazine was introduced from the formula of Klotz et al.

$$Kb = \frac{nPtKaDf - KaDfDb - Db}{BtKaDf - nPtKaDf + KaDfDb + Db} \cdot \frac{KaDf}{Db}$$

In this scheme, Ka and Kb each means the binding constant of the compound 1 and chloropromazine, Pt and Bt each means the total concentration of $\alpha_1$-AG and chloropromazine, n means the number of binding site. Df and Db each means the concentration of free and binding form of the compound 1, which were obtained when chloropromazine was added in Experiment 3. The binding constant of chloropromazine is shown in Table 3.

EXAMPLE 12

As for the other basic drugs shown in Table 3, binding constant were obtained according to the same manner as in Example 11. The result is shown together in Table 3.

TABLE 3

| Drug | log Kb |
|---|---|
| Chloropromazine | 6.46 |
| Amitriptyline | 5.58 |
| Imipramine | 5.61 |
| Trimipramine | 5.54 |
| Desipramine | 4.86 |
| prochlorperazine | 6.24 |
| Levomepromazine | 6.01 |
| Promethazine | 4.94 |
| Quinidine | 6.18 |
| Diltiazem | 5.40 |
| Pindolol | 5.33 |
| Nicardipine | 6.78 |
| Lidocaine | 5.12 |
| propranolol | 5.85 |
| Dilevalol | 4.69 |

We claim:

1. A compound of the following formula:

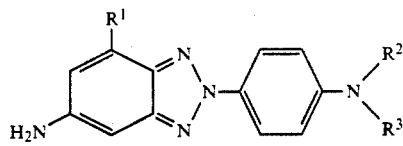

wherein R$^1$ is hydrogen, lower alkyl, halogen, cyano, or lower alkyloxycarbonyl, R$^2$ and R$^3$ each is lower alkyl, C$_3$-C$_7$ cycloalkyl, or phenyl which is unsubstituted or is substituted by one or two substituents from the group consisting of methyl or chlorine, or a salt thereof which is soluble in a solution for the determination of the binding strength of a drug to protein.

2. A compound according to claim 1 wherein R$^1$ is chlorine and R$^2$ and R$^3$ is each ethyl.